(12) United States Patent
Jehle et al.

(10) Patent No.: US 9,700,388 B2
(45) Date of Patent: Jul. 11, 2017

(54) ONE-PART OR MULTI-PART IMPLANT SYSTEM COMPRISING A MOUNTING ELEMENT HAVING ONE OR MORE OUTER RINGS

(71) Applicant: Heraeus Kulzer GmbH, Hanau (DE)

(72) Inventors: Thomas Jehle, Landeck (AT); Otmar Siegele, Kappl (AT)

(73) Assignee: HERAEUS KULZER GMBH, Hanau (DE)

( * ) Notice: Subject to any disclaimer, the term of this patent is extended or adjusted under 35 U.S.C. 154(b) by 37 days.

(21) Appl. No.: 14/649,741

(22) PCT Filed: Nov. 7, 2013

(86) PCT No.: PCT/EP2013/003349
§ 371 (c)(1),
(2) Date: Jun. 4, 2015

(87) PCT Pub. No.: WO2014/090358
PCT Pub. Date: Jun. 19, 2014

(65) Prior Publication Data
US 2016/0015484 A1 Jan. 21, 2016

(30) Foreign Application Priority Data

Dec. 11, 2012 (DE) .......... 10 2012 024 230
Feb. 13, 2013 (DE) .......... 10 2013 002 517

(51) Int. Cl.
*A61C 8/00* (2006.01)
*A61C 13/265* (2006.01)

(52) U.S. Cl.
CPC ............ *A61C 8/0059* (2013.01); *A61C 8/005* (2013.01); *A61C 8/0053* (2013.01);
(Continued)

(58) Field of Classification Search
CPC ..... A61C 8/0059; A61C 8/0018; A61C 8/005; A61C 8/0068; A61C 8/0078;
(Continued)

(56) References Cited

U.S. PATENT DOCUMENTS 6,299,447 B1  10/2001  Zuest et al.
7,704,076 B2 *  4/2010  Mullaly ............... A61C 8/0018
                                              433/172
(Continued)

FOREIGN PATENT DOCUMENTS

DE   19644333 A1   4/1998
EP   0445667 A2    9/1991
(Continued)

OTHER PUBLICATIONS

Page 3 of German Office Action for application 10 2012 024 230.1.
(Continued)

*Primary Examiner* — Glenn Richman
(74) *Attorney, Agent, or Firm* — Norris McLaughlin & Marcus PA

(57) ABSTRACT

The present invention relates to a mounting element (10) for fixing removable tooth prostheses which are anchored by an implant, comprising a lower end (13) for fastening the mounting elements (10) having an implant (21) or abutment; and an upper end for connecting the mounting element having a tooth prosthesis, optionally a friction insert; characterised in that the main body of the mounting element (10) has an outer ring (11).

21 Claims, 6 Drawing Sheets

(52) U.S. Cl.
CPC .......... *A61C 8/0066* (2013.01); *A61C 8/0068* (2013.01); *A61C 8/0072* (2013.01); *A61C 8/0018* (2013.01); *A61C 8/0078* (2013.01); *A61C 13/2656* (2013.01)

(58) Field of Classification Search
CPC ... A61C 8/0053; A61C 8/0066; A61C 8/0072; A61C 13/2656
See application file for complete search history.

(56) References Cited

U.S. PATENT DOCUMENTS

| | | | | |
|---|---|---|---|---|
| 8,764,445 B1 * | 7/2014 | DeLuca | ................ | A61C 8/005 433/173 |
| 8,920,170 B2 * | 12/2014 | Krivoruk | ............ | A61C 8/0048 433/172 |

FOREIGN PATENT DOCUMENTS

| | | |
|---|---|---|
| EP | 2366360 A1 | 9/2011 |
| WO | 2006138351 A2 | 12/2006 |
| WO | 2011027230 A2 | 3/2011 |

OTHER PUBLICATIONS

International Search Report for PCT/EP2013/003349 dated Feb. 20, 2014.

* cited by examiner

ONE-PART OR MULTI-PART IMPLANT SYSTEM COMPRISING A MOUNTING ELEMENT HAVING ONE OR MORE OUTER RINGS

This application is a §371 of PCT International Patent Application No. PCT/EP2013/003349, filed Nov. 7, 2013, which claims foreign priority benefit under 35 U.S.C. §119 of German Patent Application No. 10 2012 024 230.1, filed Dec. 11, 2012, and German Patent Application No. 10 2013 002 517.6, filed Feb. 13, 2013, the disclosures of which patent applications are incorporated herein by reference.

The invention relates to a one- or multi-part dental implant system having a mounting element. Furthermore, the invention relates to mounting elements for affixing implant-anchored removable dental restorations.

PRIOR ART

Amongst the range of embodiments, dental restorations for teeth that are completely missing or to be partially replaced consist of a dental implant system which includes an implant and optional mounting parts, and a dental prosthesis. In this context, the dental implant and the dental prosthesis assume the functions of the root of the tooth and of the occlusal surface of the tooth, respectively. Implants can take all kinds of shapes. However, conical and cylindrical implants have become predominant in practical application. In this context, these implants preferably differ in their taper and their external thread, such as, e.g., in the case of CAMLOG® SCREW-LINE implants, CAMLOG® ROOT-LINE implants, and in the series of Strauman SLA® and SLActive® implants.

A distinction is made between fixed and removable dental restorations. The stability and problematic cleaning options of fixed dental restorations contrast with the excellent cleaning capabilities and poor stability of removable dentures. These two properties can be beneficially combined through the use of a combined dental restoration. Said combined dental restorations consist of a dental prosthesis, which is mounted, through a plug connector mechanism, on the dental implant that is affixed to the jaw. Established plug mechanisms according to the prior art include, e.g. the ball-head connection element, plug bridge systems or male mould-female mould plug connector systems such as the Locator-System (US 2004/0005530; U.S. Pat. Nos. 6,299,447; 6,030,219).

In all three different connection systems, the distance of the dental prosthesis to the bone and/or the bridging of the biologic width, i.e. the distance between the lowest point of the gingival sulcus and the start of the jaw bone is defined by the length of the mounting element. In this area, the mounting elements have a smooth surface and usually consist of titanium (WO 2008/079699; EP 0 437 031). Titanium is known to be a very biocompatible metal that facilitates the attachment of organic material. As a side effect, pathogenic germs can also attach to the titanium surface of the mounting element and cause inflammation in this site. Furthermore, a gingival sulcus situated between the surface of the mounting element and the gingiva may form or an existing gingival sulcus may widen and get longer. Bacteria present in the saliva may penetrate along the gingival sulcus into the space between the surface of the mounting element and the gingiva up to the surface of the jaw bone and cause plaque and ensuing inflammation in this site. An inflammation of this type may result in loosening and complete loss of a dental implant.

Dental implants have to be adapted to the different conditions in the oral space. Accordingly, not only different angulations between the root and the crown of the tooth, but also gingival margins differing in height may be found in a tooth. For example, the gingival margins touching against the inside of the row of teeth, are higher, on average, than those touching against the outside of the row of teeth.

The mounting elements can take a large variety of shapes. Well-established in practical application are cylindrical (Straumann RN PLAN LOCATOR®) or cylinder-derived shapes such as cylinders with strongly rounded corners (Straumann WN PLAN LOCATOR®) and variable diameter (Straumann WN PLAN Massivsekundärteil 6°.

Document EP 2 366 360 discloses a dental implant system that consists of an implant, a screw-on mounting element with a plug connector for the dental prosthesis at the upper end of the mounting element. Said dental implant system is associated with typical problems related to bacteria. Accordingly, the implant usually loosens in the course of healing, because the tension originally produced by the screw connection is reduced by the bone. Only then, complete ingrowth and healing commence. During this time, the gap between the implant and the bone is susceptible to bacterial infestation and gingival proliferation. Furthermore, the gingival sulcus is also always susceptible to bacterial infestation above the implant, i.e. between the gingiva and the mounting element. Both types of infection can lead to loss of the implant.

Document DE 196 44 333 discloses a membrane on the upper end of the implant. This separate membrane closes the bone gap between the implant and the bone, thereby preventing the ingress of bacteria or gingiva. However, this membrane does not prevent the ingress of bacteria into the gingival sulcus either. Furthermore, this document does not provide a general teaching from which a solution to the problem of the ingress of bacteria into the gingival sulcus could be derived, as the membrane solution requires phases that are as firm and rigid against each other as possible, such as, e.g., the bone and the implant.

Document EP 0 445 667 discloses semiconducting and thus high ohmic resistance materials, such as, e.g., zirconium oxide, as inhibitors of plaque and bacteria formation in the form of a surface layer on implant and mounting element. However, EP 0445667 does not completely solve the problem of bacterial ingress into the gingival sulcus.

It is therefore the object of the invention to provide a dental implant system for affixing removable dental restorations, wherein the dental implant system contains a mounting element that minimises and partially prevents the accumulation and advance of bacteria present in saliva to the bone boundary of the artificial root. In addition, the necessary angulation of the mounting element for implants or abutments is to be solved integrally, i.e. without additional elements.

The invention is based on the finding that the advance of bacteria present in the saliva to the bone boundary is reduced when a mounting element having an outer ring is used such that the biological width of the gingiva is provided by the jaw bone up to at least just above said outer ring. The invention is further based on the finding that an angled mounting element enables a simplified adaptation of implants or abutments to the existing needs, which are defined by the jaw and tooth position. Previous implants could compensate for angular differences of 10° (historically also up to 20°) in that the shear forces were absorbed by the material primarily at the female mould-male mould connection. This resulted in higher wear of the implants. Accordingly, the shelf life of the implant can be extended significantly through the use of angled mounting elements. Furthermore, different coupling levels can be balanced by angled mounting elements and thus tailor-made mounting elements can be produced for all possible tooth positions. Regardless, the invention is based on the finding that different heights of gingiva can be present in the oral space (sides of the row of teeth facing and facing away from the oral space) and that this height of the gingiva in contact can be varied via the height of the outer rings.

The invention provides a:
mounting element for affixing implant-anchored removable dental prostheses, containing
a lower end for attachment of the mounting element to an implant or abutment;
an upper end for connecting the mounting element to a dental prosthesis, optionally a friction insert; wherein
the base body of the mounting element comprises an outer ring.

A preferred embodiment of the invention is a non-angled mounting element having at least one outer ring, which may have an angulation or no angulation. Moreover, all combinations of outer rings with and without angulation are feasible. The outer rings can have one or more gaps.

A further preferred embodiment of the invention is an angled mounting element having at least one outer ring, which may have an angulation or no angulation. Moreover, all combinations of outer rings with and without angulation are feasible. The outer rings can have one or more gaps.

All artificial components that ensure the restoration of lost natural tooth functions are called dental restoration. In addition to fixed and removable dental restorations, there are combined dental restorations. Combined dental restorations is composed of an implant system and an affixable dental prosthesis. In this context, the affixable component is mounted, in removable manner, on the component fixed in the jaw by means of a connection mechanism.

An implant system comprises the implant and all other parts which are necessary in order to mount the dental prosthesis. In a one-part implant system, no further parts are required, since the dental prosthesis is mounted directly on the implant. A multi-part implant system comprises the implant, at least one abutment, and at least one mounting element. In a multi-part implant system, the implant is preferably connected via an abutment and a mounting element.

An implant is the support of the dental prosthesis and an artificial replacement of the natural tooth root. Its function is to anchor the dental prosthesis in the jawbone. In a one-part implant system, the implant is a solid body that bears the dental prosthesis, and is fixed directly in the jawbone. In a multi-part implant system, the implant is a hollow body that is fixed in the jawbone, in which an abutment is attached, on which a mounting element is mounted.

The mounting element is a solid or hollow body and may comprise, on its upper end, an incorporated male mould or female mould.

The abutment is a solid or hollow body with an abutment plate at the upper end.

The upper end of all parts described herein always means the end which is closer to the attached dental prosthesis and/or is closer to the receptacle for the tooth prosthesis.

The lower end of all parts described herein always means the end which is closer to the implant.

A female mould is a free-form incorporated into a workpiece that can form a mechanical connection to a complementary male mould in that the female mould surrounds the male mould on the outside in a perfectly fitting manner.

A male mould is a free-form incorporated into a workpiece that can form a mechanical connection to a complementary female mould in that the male mould fits into the inside of the female mould in a perfectly fitting manner.

An outer ring is a three-dimensional body that is a concentric mounting bulge along the outside of the base body of the mounting element. The outer ring is characterised by its width and its height, as well as its distance, optionally mean distance, from the lower end of the base body of the mounting element, as well as the angulation with respect to the lower side of the mounting element.

The angulation of the outer ring is present when the plane formed by the outer ring and the coupling plane at the lower end of the base body are not parallel to each other.

The widest site of the outer ring is the position at which the outer ring has its maximal effective diameter.

The effective diameter is the diameter of a cylindrical shape. In case the cross-sectional surface is non-circular, the effective diameter is the diameter that corresponds to the diameter of a circular cross-sectional surface of the same surface area.

The width of the outer ring is the distance from the widest site of the outer ring to the base of the outer ring which corresponds to the surface of the mounting element.

The height of the outer ring is the distance, in the cross-section of the mounting element, between the two points at which the outer ring has a larger effective diameter than the base body of the mounting element, but at the same time has the smallest effective diameter in the entire outer ring.

A cap is a sleeve that is closed on one side.

A friction insert is a wearing part that is closed on top and made of elastic polymer having a female mould or a male mould incorporated on the open side.

A gingival sulcus (Sulcus gingivae) is an angled gap between the surface of the base body of the mounting element and the adjacent gingiva. The gingival sulcus may extend all the way to the jawbone.

A recess is the reduction at a point or along a line of a three-dimensional body that results in a concavity being formed on the surface.

A base body is a three-dimensional form that provides core features that are retained in all forms derived from it.

An angulation of the base body is evident and the base body is angled if the surfaces on the upper and on the lower end of the body are not parallel to each other. Dental restorations are sub-divided into three different compositions of parts which can artificially assume the natural tooth function. Such compositions can be fixed, removable or be a combination of these two properties. Embodiments include crowns, bridges or dental prostheses. In a combined dental restoration, an implant is attached in the jaw and has a dental prosthesis removably affixed to it by a connection mechanism (ball head, connector strip, Locator, etc.). Combined dental restorations impart stability on the removable dental prosthesis with respect to implants affixed in the jaw by means of this connection mechanism and also improve the hygiene through the option of removing the dental prosthesis.

An implant system refers to all components that are necessary to secure a dental prosthesis in the jawbone. There are one-part and multi-part implant systems. One-part implant systems comprise an implant, which is a solid body and provides an implant surface that bears the dental prosthesis. Multi-part implant systems comprise an implant, which is a hollow body that bears an optional internal thread. A mounting element is mounted on the implant by means of an abutment. The dental prosthesis is attached to said mounting element.

An implant is a part anchored in the jaw and made of a biocompatible metal (e.g. titanium or a titanium alloy), and substitutes for the function of the natural tooth root by providing support and stability to the dental prosthesis mounted thereon. It can have an optional rough surface, an optional external thread, and an optional internal thread. The implant is secured in the jawbone, wherein the optional rough surface provides a stable connection to the jawbone. Implants are used in one-part and multi-part implant systems. In the one-part implant system, the dental prosthesis is firmly affixed on the implant via the implant surface, whereas a mounting element in a multi-part implant system is affixed on an abutment which is secured in an implant affixed in the jawbone. The implant is made functional in connection with the dental prosthesis, which is either affixed permanently on the implant or mounted in removable manner via a plug connection. Preferred embodiments of implants are cylindrical or conical in shape. These embodiments also include cylindrical or conical shapes with rounded edges and tips.

The mounting element consists of titanium, a titanium alloy or a ceramic material and has an optional male mould or female mould incorporated at the upper end of its solid or hollow body. The mounting element of one-part implant systems is affixed permanently on the implant surface. The mounting element of multi-part implant systems is affixed permanently on the abutment, specifically on the abutment plate, and screw-retained to the implant by means of the abutment in removable manner. The mounting element is the connector unit to the permanently or removably affixed denture. In case of a removable fixation, common forms for said type of fixation are incorporated at the upper end of the mounting element, such as, e.g., a ball head, a female mould or male mould. Preferred embodiments of mounting elements are cylindrical in shape. These embodiments also comprise cylindrical shapes with rounded edges. An angled mounting element allows for the mounting of an angled connection of implant or abutment to a dental prosthesis, optionally to a friction insert. In this respect, the relative position of the two elements to be connected (implant and dental prosthesis) determines the angulation of the mounting element and/or, of the base body. Usually, it is easy to determine, in thought, a coupling plane that is orthogonal to the longitudinal axis of the implant and/or abutment and is situated at the upper end of the mounting element. Likewise, it is easy to determine, in thought, a second coupling plane that is orthogonal to the longitudinal axis of the connection element of the dental prosthesis and is situated at the lower end of the mounting element. An angulation is present when the coupling planes are not parallel to each other. The outer shape of the base body is thus irrelevant for the definition of an angulation of the mounting element and/or base body except the provision of said coupling planes.

Abutments that are particularly well-suited for the invention have an anti-rotation mechanism in order to provide for a fixed position of the mounting element in the oral space and to prevent a rotation of the mounting element on the abutment. Said anti-rotation mechanism consists mainly of a groove milled on the inside of the mounting element along the longitudinal axis and of a spring fitting the groove perfectly, which are pushed into one another during connection, and prevent rotation. Examples of said abutments include the HEX abutments of Zirkonzahn®, e.g. CAM-LOG®-J-TYPE/K-TYPE HEX or FRIADENT DENTSPLY-XiVE® HEX.

The abutment is made of titanium, a titanium alloy or a ceramic material, and has an abutment plate at the upper end of its solid or hollow body. The mounting element is affixed to the abutment plate. The abutment is fastened in the implant, e.g. screwed by an abutment screw into the optional internal thread of the implant, and serves as a removable connecting element between mounting element and implant. Preferred embodiments of abutments are cylindrical in shape. These embodiments also comprise cylindrical shapes with rounded edges.

A female mould is a free-form that is being incorporated into a workpiece, and can be connected to a complementary free-form, the male mould, in removable manner. A female mould of this type is used in the Locator-System and enables a detachable plug connection. The female mould is incorporated either on the upper side of the mounting element or on the underside of the cap and/or of the friction insert. The mounting element and the dental prosthesis are preferably connected by means of a friction insert.

A male mould is a free-form that is being incorporated into a workpiece, and can be connected to a complementary free-form, the female mould, in removable manner. A male mould of this type is used in the Locator-System and enables a detachable plug connection. The male mould is incorporated either on the upper side of the mounting element or on the underside of the cap and/or of the friction insert. The mounting element and the dental prosthesis are preferably connected by means of a friction insert.

An outer ring is located on the outside of the mounting element and is characterised by means of its width and its height, as well as its distance from the lower end of the solid or hollow body of the mounting element. In this context, the distance from the lower end of the mounting element can be constant in all sites, but can just as well comprise a largest and a smallest distance of all distances. Furthermore, the outer ring can comprise one or more gaps, i.e. the bulge of the outer ring on the surface of the mounting element need not be continuous. Since the outer ring is directly incorporated in the solid or hollow body of the mounting element, it consists of the same material, such as, e.g., titanium, a titanium alloy or a ceramic material. Mounting elements comprising one or two outer rings increase the connective tissue compatibility of the mounting element with respect to the mucosa of the adjacent gingiva and reduce the formation of gingival sulci, and thereby the accumulation of plaque with embedded bacteria, the development of inflammation, and ultimately the premature loss of the implant. In an angled outer ring, the outer ring has a non-constant distance from the lower end of the mounting element. Said angled outer ring enables the mounting of various gingival heights around the mounting element. Usually, it is easy to determine, in thought, a coupling plane that is orthogonal to the longitudinal axis of the implant and/or abutment and is situated at the lower end of the mounting element. Likewise, it is easy, in thought, to determine a plane that corresponds to the surface of the outer ring. An angulation of the outer ring is present when the coupling plane and the plane of the outer ring are not parallel to each other.

The widest site of the outer ring is the position at its surface that comprises its maximal effective diameter.

The width of the outer ring corresponds to the distance along the vertical line from the widest site of the outer ring to the height of the surface of the mounting element.

The height of the outer ring corresponds to the distance between two points in the cross-section of the outer ring between which the widest site of the outer ring is located and which have a wider effective diameter than the mounting element, but have the smallest effective diameter in the entire outer ring.

The distance of the outer ring to the lower end of the mounting element corresponds to the shortest distance between the lower end of the mounting element and a point situated between the lower end of the mounting element and the widest site of the outer ring and which has a wider effective diameter than the mounting element, but has the smallest effective diameter in the entire outer ring.

The mean distance of the outer ring is half of the sum of the smallest and of the largest distance of the outer ring to the lower end of the mounting element. For mounting elements with outer rings with a constant distance from the lower end of the mounting element, the mean distance and the distance from the lower end of the mounting element are identical.

A cap is a hollow body made of titanium, a titanium alloy, or a ceramic material (e.g., zirconium oxide) with a closed side. The dental prosthesis is affixed permanently to the cap and the cap can bear a friction insert at the underside. If no friction insert is present, a connection element, such as a female mould or male mould, can be incorporated into the cap.

A friction insert consists of an elastic polymer and forms, on one side, the negative mould of the cap, into which it fits. A female mould or male mould can be incorporated on the open side of the friction insert. The friction insert is affixed in the cap and serves to define the action point of the removable plug connection between mounting element and dental prosthesis. The mounting element and the dental prosthesis are preferably connected by means of a friction insert.

A gingival sulcus (Sulcus gingivae) is the opening between the surface of the mounting element and the adjacent gingiva. Bacteria can accumulate in a gingival sulcus, which can lead to inflammation and further opening of the gingival sulcus up to the jawbone surface. Such inflammation can lead as far as to premature loss of the implant. A sulcus depth of more than 2 mm is considered pathological.

A base body provides core features of a three-dimensional form that are retained in all embodiments derived from it. For example, a mounting element comprises a cylinder as a base body, wherein one embodiment can be a solid cylinder, while another can be a hollow cylinder with a particular wall thickness.

A recess is the depression in the surface between two outer rings. In this context, the effective diameter of the mounting element at the widest sites of the outer rings is larger than at any point of the recess between the outer rings.

In contrast to conventional mounting elements, no gap can form in the present invention between the gingiva and the mounting element, which opens up to the surface of the jawbone. The application of an outer ring reduces the ingress of bacteria between gingiva and mounting element, possibly extending up to the bone surface, as compared to mounting elements having no outer ring.

An object of the invention is a mounting element for affixing implant-anchored removable dental prostheses, containing a lower end for attachment of the mounting element to an implant or abutment; an upper end for connecting the mounting element to a dental prosthesis, optionally a friction insert; characterised in that the base body of the mounting element comprises an outer ring, wherein the base body of the mounting element is angled, and wherein the base body of the mounting element comprises a second outer ring positioned appropriately below the first outer ring on the base body such that a recess is formed around the base body between the first outer ring and the second outer ring. In particular the base body of the mounting element is not angled and comprises an angled outer ring.

The mounting element preferably has a solid or hollow body having an effective diameter of 1.5 mm to 10 mm, preferably 2 mm to 8 mm, more preferably 2.5 mm to 7 mm, most preferably 3 mm to 6 mm.

The mounting element preferably has an outer ring with a width of 0.1 mm to 5.0 mm, preferably 0.2 mm to 3.0 mm, more preferably 0.5 mm to 2.0 mm, most preferably 0.7 mm to 1.5 mm.

The mounting element preferably has an outer ring with a height of 0.1 mm to 3 mm, preferably 0.5 mm to 2.5 mm, most preferably 1 mm to 2 mm.

The non-angled outer ring of a mounting element has an angulation of 0°.

The angled outer ring of a mounting element has an angulation of 1° to 40°, more preferably of 3° to 25°, and most preferably of 5° to 15°. The angulation of the outer ring is specified in positive angle values only. Since the angulation of the outer ring is independent of the angulation of the mounting element, all possible combinations of angles are feasible. The embodiment, in which the two angulations occur in opposite directions, i.e., the side of the largest distance of the outer rings from the lower end of the mounting element is situated exactly opposite to the side with the largest angulation of the mounting element, is preferred.

The base body of the angled mounting element has an angulation with an angle of 5° to 50°, preferably of 7° to 40°, more preferably of 8° to 30°, and most preferably of 9° to 20°.

The implant is preferably installed appropriately such that the outer ring of the mounting element is being positioned between the jawbone surface and the deepest site of the gingival sulcus, i.e. within the biological width.

The mounting element preferably has a mean distance between the lower end of the outer ring and the lower end of the mounting element of 0.3 mm to 7 mm, preferably 0.4 mm to 6 mm, most preferably 0.5 mm to 5 mm. Moreover, it can be advantageous that the distance is not equal at all sites. It has been evident that the outer ring, in the installed position, can rest higher on the side facing the oral space and rest lower on the side facing away from the oral space.

The base body of the mounting element preferably possesses a second outer ring below the first outer ring on the surface, wherein a recess is formed around the solid or hollow body between the first and the second outer ring. Much like the first outer ring, the second outer ring can comprise a smallest and a largest distance from the lower end of the mounting element.

The mounting element preferably has a second outer ring having the same dimensions as the first outer ring.

The mounting element preferably has a distance between the widest sites of the two outer rings of 0.1 mm to 5 mm, more preferably 0.5 mm to 4 mm, most preferably 1 mm to 3 mm.

Moreover, it is preferred that the distance of the widest sites of the two outer rings is constant over the entire region of the outer rings.

The mounting element preferably has a height of 1 mm to 15 mm, more preferably 2 mm to 12 mm, most preferably 3 mm to 9 mm.

The material of the mounting element preferably comprises ceramic material. Zirconium oxide ($ZrO_2$) is particularly preferred.

In particular, the surface of the mounting element is preferred to consist of zirconium oxide ($ZrO_2$).

It is particularly preferred to provide the surface to be made of zirconium oxide ($ZrO_2$) in the range of the biological width D.

The mounting element preferably has a female mould or a male mould incorporated into its upper end.

In a preferred embodiment of the invention, the mounting element is designed as a hollow body and the mounting element is preferably fastened to the implant via an abutment, which is screwed to the implant by a screw extending through the interior of the mounting element.

In an embodiment of the invention that is also preferred, the mounting element comprises a solid body that comprises an external thread for fastening the mounting element in the implant.

The invention further relates to a one-part implant system for anchoring of removable dental prostheses, which contains an implant for fastening the implant system in a jawbone or the root of a tooth, an implant surface as the upper end of the implant, and a mounting element fastened on the implant surface.

Moreover, the invention relates to a multi-part implant system for anchoring of removable dental prostheses, containing an implant for insertion into a jawbone or a root of a tooth, an abutment having a stem for fastening the abutment in the implant, an abutment plate at the upper end of the stem, and a mounting element fastened on the abutment plate.

A further preferred embodiment of the invention comprises a one-part or multi-part implant system, in which the mounting element is screwed to the implant surface or abutment plate.

A preferred use of the invention comprises the minimisation and partial prevention of the ingress of bacteria present in the saliva in the gingival sulcus and/or prevention of the expansion of the gingival sulcus and/or compensation of different gingival levels in the context of one- or multi-part dental implants through mounting elements with one or two outer rings.

LIST OF REFERENCE NUMBERS

Figure 1:
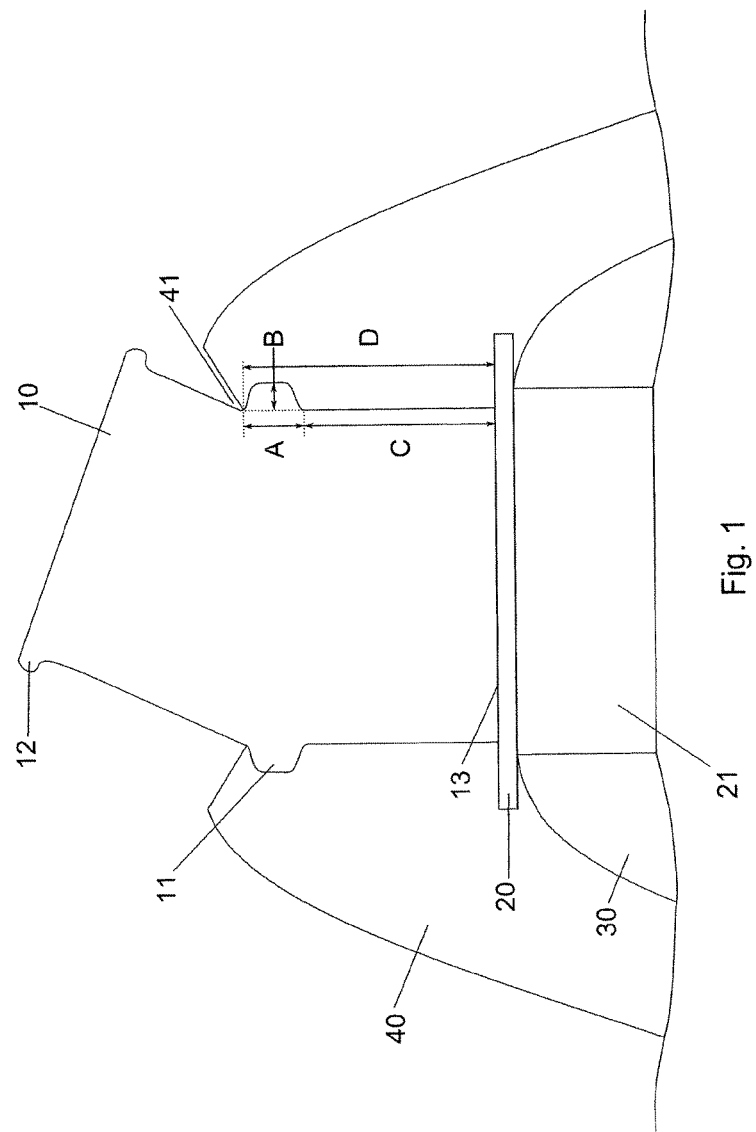
FIG. 1: Implant mounting element, base body with one outer ring, implant mounting element designed as male mould

10 Implant mounting element
11 First outer ring
12 Male mould
13 Lower end of implant mounting element
14 Female mould
15 Second outer ring
16 Recess between the two outer rings
17 Angulation of the base body of the mounting element
18 Angulation of the outer ring
20 Implant surface or abutment plate
21 Implant
22 Abutment
23 Abutment screw
24 Friction body
25 External thread
26 Cap
30 Jawbone
40 Gingiva
41 Sulcus gingivae/gingival sulcus
A Height of outer ring
B Width of outer ring
C Distance of lower edge of the outer ring from the lower end of the implant mounting element
D Biological width/Distance of the lowest site of the gingival sulcus from the jawbone
E Distance between the widest sites of the two outer rings
Embodiments of the Invention In general, figures bearing a '*' following the number of the figure, i.e. FIGS. 1*, 2*, 3*, 4*, 5*a-e, show the same as figures without the '*', but show an embodiment having a non-angled building element.

FIG. 1 shows a one-part or multi-part implant system that is anchored in the jawbone 30 and mounted on an angled mounting element 10. Said mounting element 10 has an outer ring 11 of width B and height A, wherein width and height are of the same order of magnitude. The position of the outer ring 11 is defined by the biological width D and the distance C of its lower end to the abutment plate or implant surface 20 and/or the lower end of the mounting element 13. The gingiva 40 touches against the mounting element 10 above the outer ring and has only a small gingival sulcus 41. A male mould is incorporated at the upper end of the mounting element 10.

Figure 2:
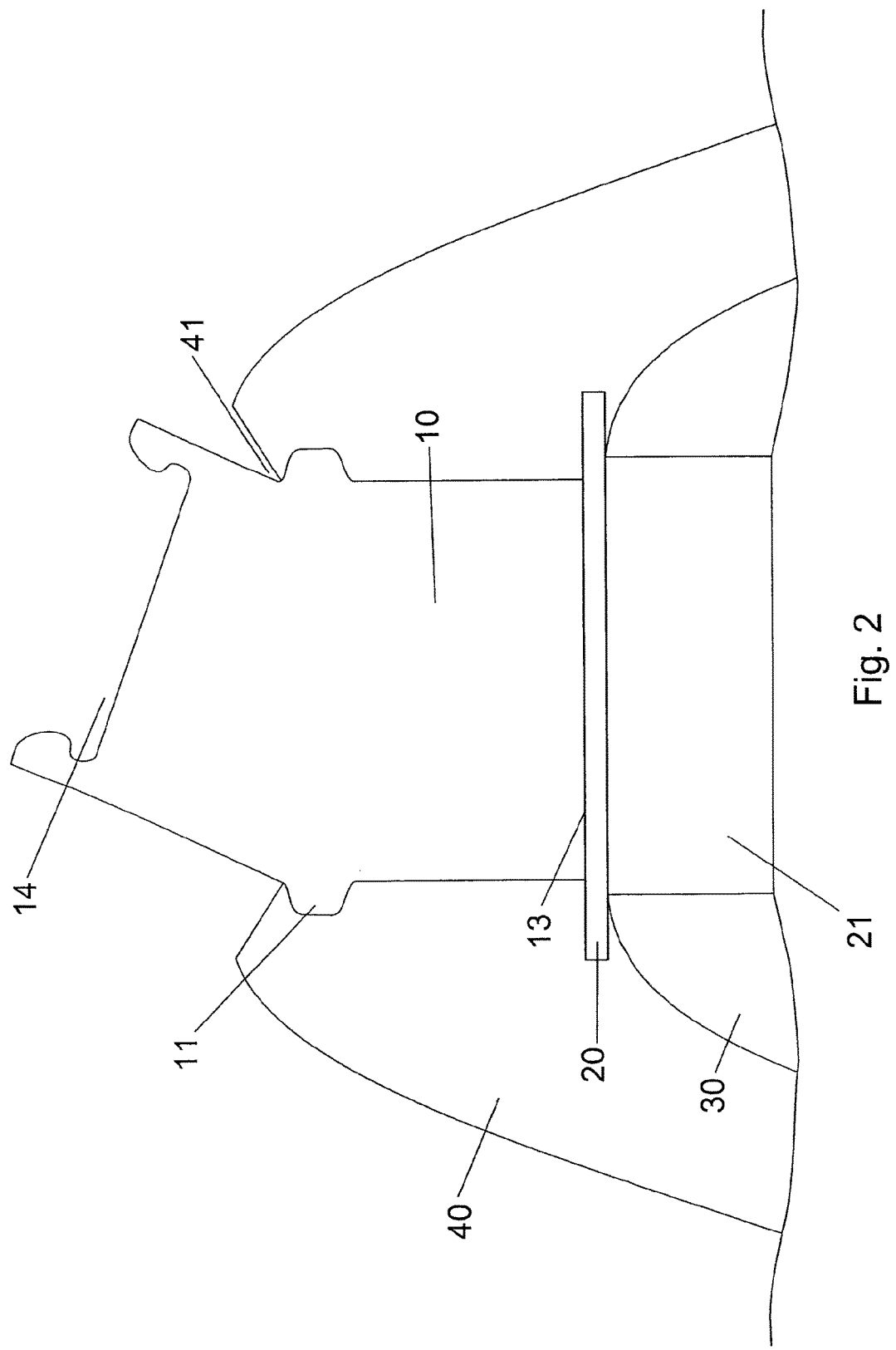
FIG. 2: Implant mounting element, base body with one outer ring, implant mounting element designed as female mould

FIG. 2 shows a one-part or multi-part implant system that is anchored in the jawbone 30 and has an angled mounting element 10 mounted, by its lower end 13, on its abutment plate or on the implant surface 20. Said mounting element 10 possesses an outer ring 11, wherein the gingiva 40 touches against the upper end thereof and has only a small gingival sulcus 41. A female mould is incorporated at the upper end of the mounting element 10.

Figure 3:
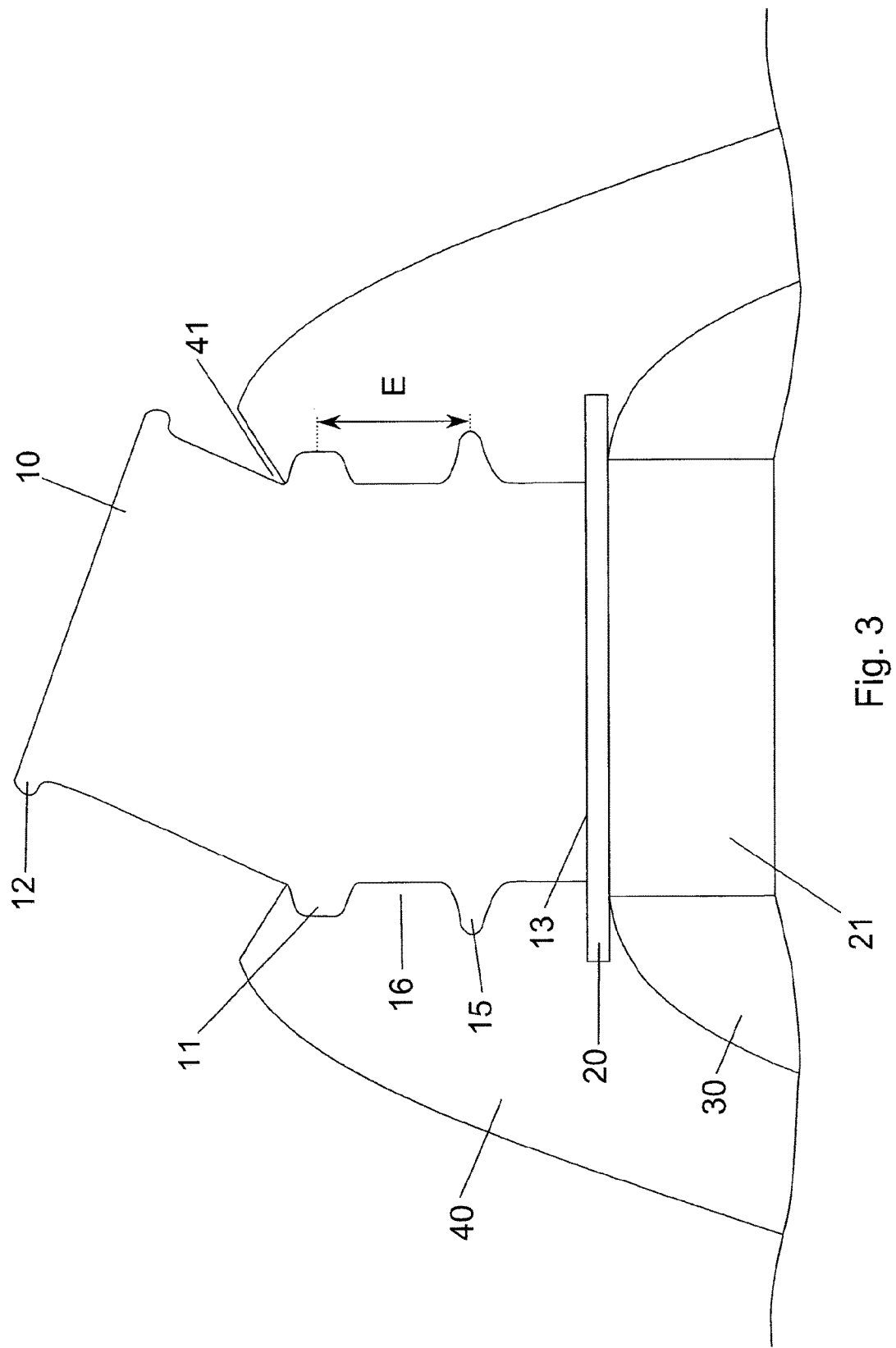
FIG. 3: Implant mounting element, base body with two outer rings, implant mounting element designed as male mould

FIG. 3 shows a one-part or multi-part implant system that is anchored in the jawbone 30 and has an angled mounting element mounted, by its lower end 13, on its abutment plate or on the implant surface 20. Aside from an outer ring 11, said mounting element possesses a second outer ring 15 situated, at the distance E to the first outer ring 11, between the first outer ring and the lower end of the mounting element 13. A recess 16 results between the two outer rings. The gingiva 40 touches against the upper end of the first outer ring 11 and forms only a small gingival sulcus 41. A male mould is incorporated at the upper end of the mounting element 10.

Figure 4:
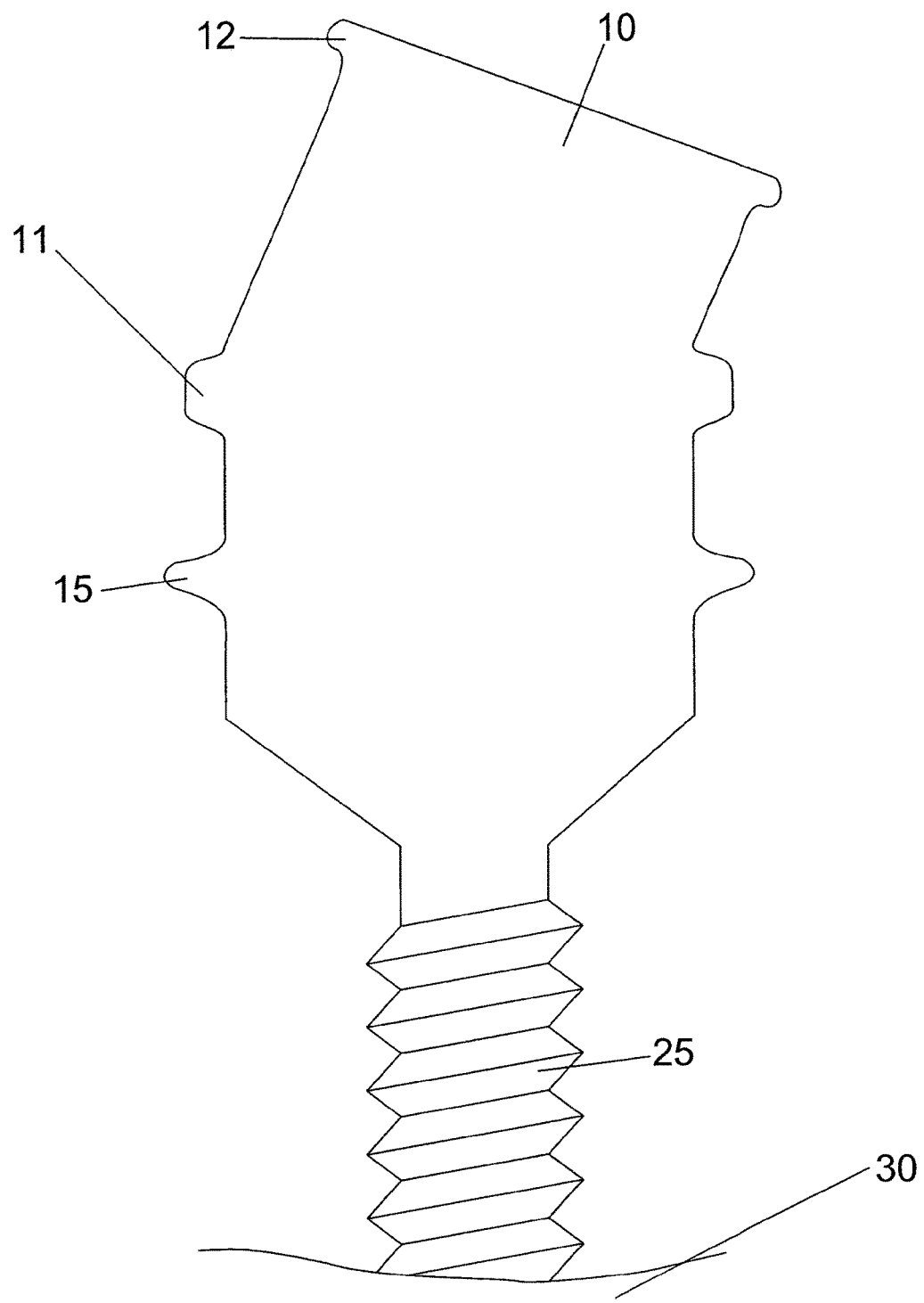
FIG. 4: Implant mounting element, designed as massive body with external thread for attachment to implant

FIG. 4 shows a one-part implant system that comprises, aside from a first outer ring 11, a second outer ring 15 at its angled mounting element 10. The mounting element is firmly affixed to the implant, which has an external thread 25. The implant is screwed into the jawbone 30 by means of said external thread 25.

Figure 5:
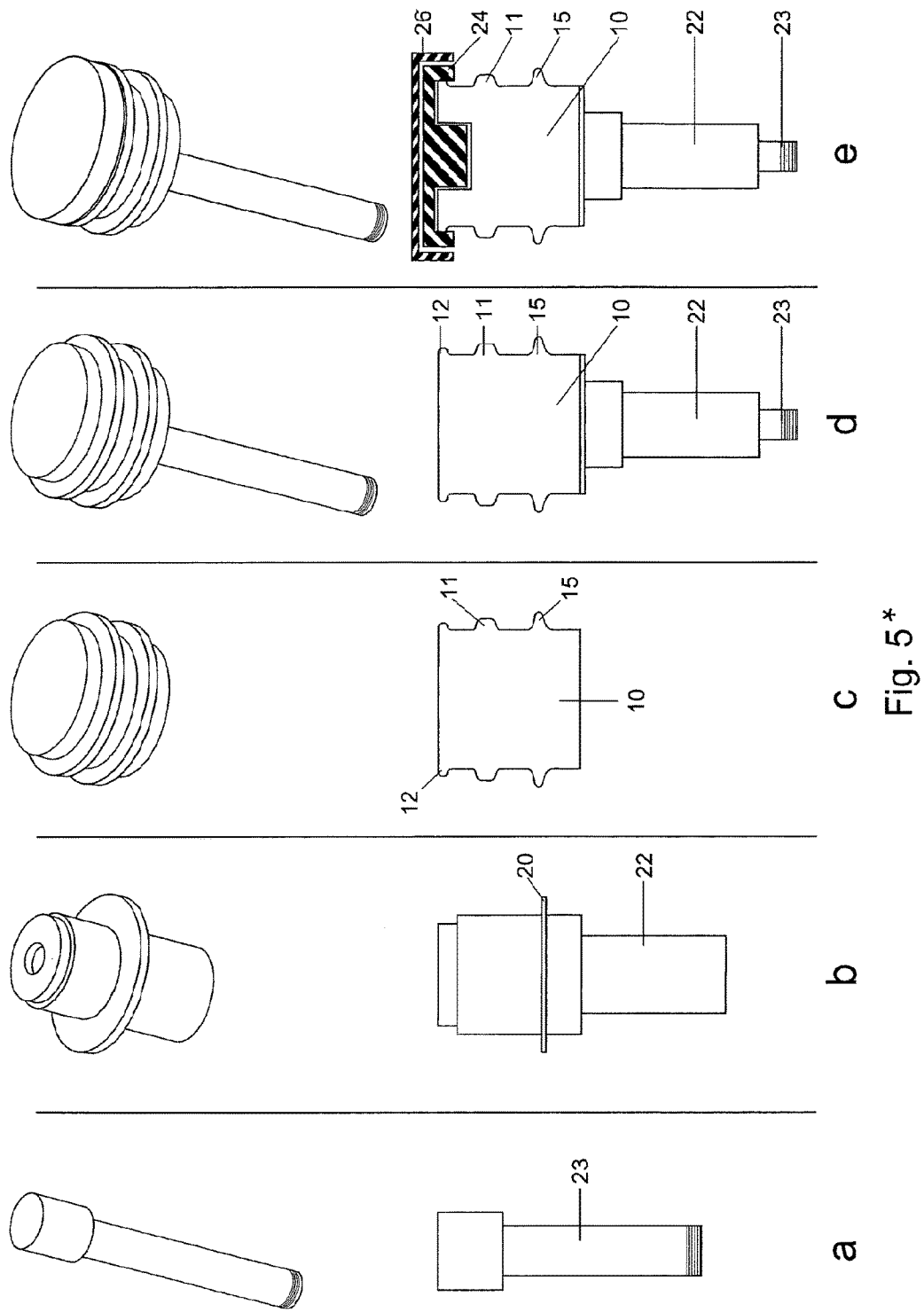
FIG. 5a-e: Implant mounting element, designed as hollow body, attachment of the implant mounting element in the implant by means of a screw

FIG. 5a corresponds to the prior art and shows a sectional and perspective view of an abutment screw 23 with an external thread at the lower end and an attachment with a larger effective diameter at the upper end, which is to prevent the abutment 22 from slipping through.

FIG. 5b corresponds to the prior art and shows a sectional and perspective view of an abutment 22 that comprises an abutment plate 20. The abutment is a hollow body and is screwed to the implant 21 by its hollow shape via the abutment screw 23 (FIG. 5a).

Figure 6:
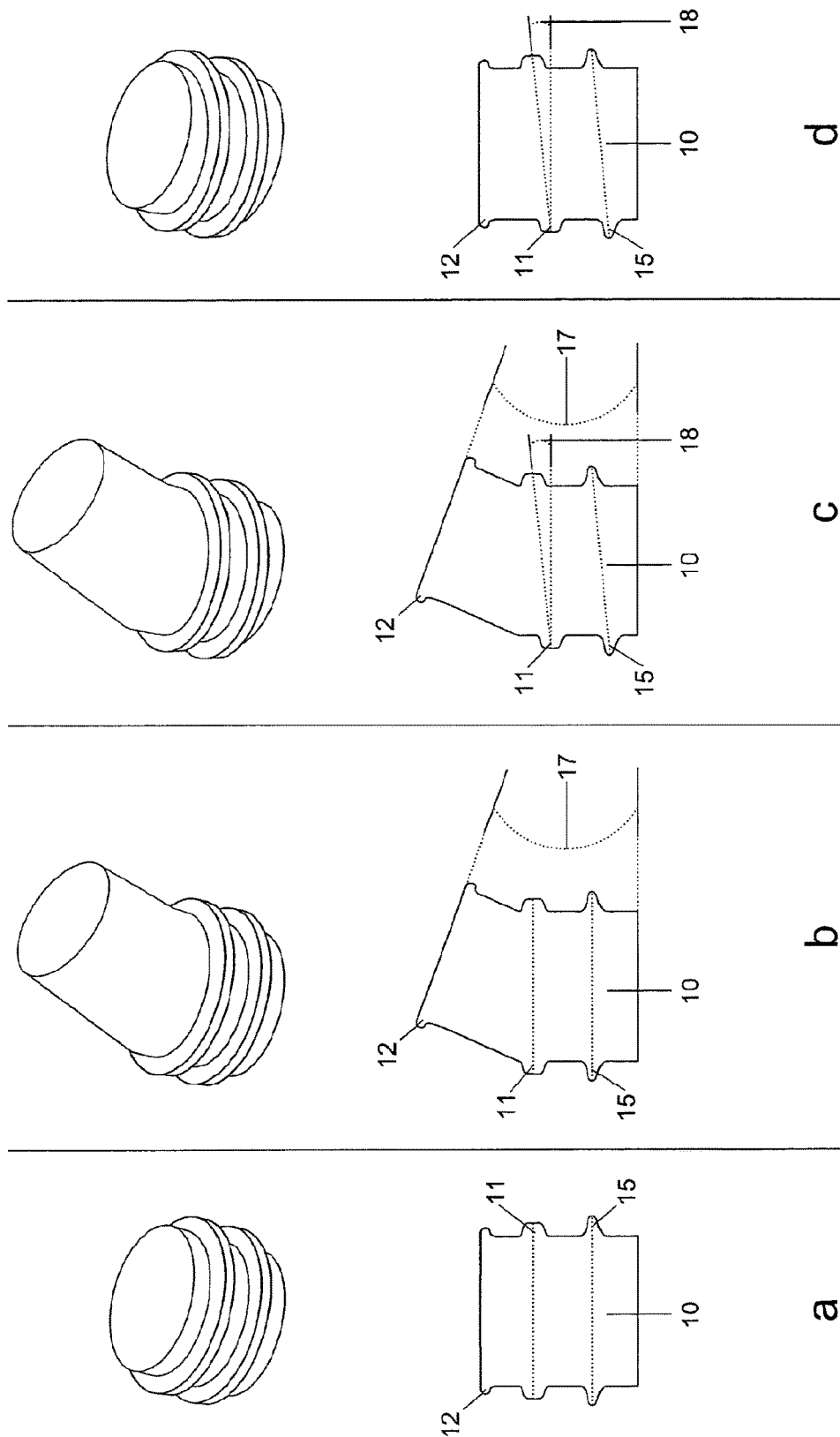
FIG. 6a-d: Implant mounting elements, various combinations of non-angled and angled base bodies and angled outer rings with constant as well as smallest and largest distance from the lower end of the mounting element.

FIGS. 5c and 6b show a sectional and perspective view of an angled mounting element 10 having the angulation 17, having a first outer ring 11, a second outer ring 15, wherein the first and second outer ring comprise a constant distance to the lower end of the mounting element and thus form an angle of 0° between the coupling plane of the lower end of the mounting element and the plane of the outer ring, as well as of a male mould 12. The mounting element 10 is affixed to the abutment 22. A dental prosthesis comprising a female mould can be connected by means of the male mould 12 in detachable manner.

FIG. 5d shows a sectional and perspective view of an angled mounting element 10 affixed on an abutment 22, in which an abutment screw 23 is inserted. The abutment 22 is shown transparent. The mounting element 10 possesses a first 11 and a second outer ring 15 and a male mould 12 at the upper end. The abutment screw 23 is situated in the hollow shape of the abutment 22 and the mounting element 10 is mounted on the abutment plate 20 of the abutment 22.

FIG. 5e shows a sectional and perspective view of an angled mounting element 10 affixed on an abutment 22, in which an abutment screw 23 is inserted. The abutment 22 is shown transparent. The mounting element 10 possesses a first 11 and a second outer ring 15 and a male mould 12 at the upper end. The abutment screw 23 is situated in the hollow shape of the abutment 22 and the mounting element 10 is mounted on the abutment plate 20 of the abutment 22. A cap 26, in which a friction insert 24 is affixed to an incorporated female mould 14, is connected to the mounting element 10, in detachable manner, by means of said female mould and the male mould of the mounting element 10.

FIG. 6a shows a sectional and perspective view of a non-angled mounting element 10 having a first outer ring 11 and a second outer ring 15, which comprise a constant distance to the lower end of the mounting element and thus form an angle of 0° between the coupling plane of the lower end of the mounting element and the plane of the outer ring, as well as of a male mould 12. The mounting element 10 is affixed to the abutment 22. A dental prosthesis comprising a female mould can be connected by means of the male mould 12 in detachable manner.

FIG. 6c shows a sectional and perspective view of an angled mounting element 10 having the angulation 17, a first outer ring 11, a male mould 12, and a second outer ring 15. In the mounting element, the largest distance from the lower end to the outer ring is in the place, at which the angulation on the base body is smallest, and, accordingly, it comprises an angulation 18 unequal to 0° between the coupling plane of the lower end of the mounting element and the plane of the outer rings 11 and 15. Moreover, in the mounting element, the distance from the lower end is smallest in the place, in which the angulation on the base body is largest. The mounting element 10 is affixed to the abutment 22. A dental prosthesis comprising a female mould can be connected by means of the male mould 12 in detachable manner.

FIG. 6d shows a sectional and perspective view of a non-angled mounting element 10 having a first outer ring 11 and a second outer ring 15, which have a largest distance from the lower end of the mounting element and a smallest distance from the lower end of the mounting element and thus form an angulation 18 unequal to 0° between the coupling plane of the lower end of the mounting element and the plane of the outer rings 11 and 15, as well as of a male mould 12. The mounting element 10 is affixed to the abutment 22. A dental prosthesis comprising a female mould can be connected by means of the male mould 12 in detachable manner.

The invention claimed is:

1. A mounting element for affixing implant-anchored removable dental prostheses, comprising a lower end for attachment of the mounting element to an implant or abutment; and an upper end for connecting the mounting element to a dental prosthesis;
   wherein
   (i) a base body of the mounting element comprises a first outer ring,
   (ii) the base body of the mounting element is angled,
   (iii) the base body of the mounting element comprises a second outer ring positioned appropriately below the first outer ring on the base body such that a recess is formed around the base body between the first outer ring and the second outer ring, and
   (iv) the widest sites of the two outer rings is separated by a distance which is constant over the entire region of the two outer rings.

2. The mounting element according to claim 1, wherein the angulation of the base body comprises an angle of 5° to 50°.

3. The mounting element according to claim 1, wherein the base body of the mounting element has an effective diameter of 1.5 mm to 10 mm.

4. The mounting element according to claim 1, wherein the first outer ring has a width of 0.1 mm to 5.0 mm, and/or a height of 0.1 mm to 3 mm, and/or comprises one or more gaps.

5. The mounting element according to claim 4, wherein the first outer ring has a height of 1 mm to 2 mm.

6. The mounting element according to claim 1, wherein the first outer ring is positioned appropriately on the mounting element such that the first outer ring, after incorporation of the implant into the jawbone, is situated in the region between the jawbone surface and the lowest site of the gingival sulcus, i.e. within the biological width.

7. The mounting element according to claim 1, wherein the mean distance between the lower end of the first outer ring and the lower end of the mounting element is 0.3 mm to 7 mm.

8. The mounting element according to claim 1, wherein the second outer ring has the same dimensions as the first outer ring.

9. The mounting element according to claim 1, wherein the distance between the widest sites of the two outer rings is 0.1 mm to 5 mm.

10. The mounting element according to claim 1, wherein the outer rings comprise no angulation, or wherein at least one outer ring comprises an angulation of 1° to 40°.

11. The mounting element according to claim 1, wherein the mounting element has a height of 1 mm to 15 mm.

12. The mounting element according to claim 1, wherein the mounting element comprises ceramics and/or has a height of 2 mm to 12 mm.

13. The mounting element according to claim 1, wherein the upper end is designed as a male mould or a female mould.

14. The mounting element according to claim 1, wherein (a) the mounting element is designed as a hollow body and the mounting element is fastened to the implant via an abutment, which is fastened on the implant by a screw extending through the interior of the hollow body, or (b) the mounting element is designed as a massive body and comprises an external thread for fastening the mounting element to the implant.

15. The mounting element according to claim 1, wherein the abutment is provided with an anti-rotation mechanism.

16. The mounting element according to claim 15, wherein the anti-rotation mechanism consists of a groove milled on the inside of the mounting element along the longitudinal axis and of a spring that fits the groove perfectly, which are pushed into one another during connection.

17. An one-part implant system for anchoring of removable dental prostheses, comprising an implant for fastening the implant system in a jawbone or in a root of a tooth; an implant surface as upper end of the implant; and the mounting element according to claim 1 fastened on the implant surface.

18. A multi-part implant system for anchoring of removable dental prostheses, comprising an implant for insertion into a jawbone or a root of a tooth; and an abutment having a stem for fastening the abutment in the implant, an abutment plate at the upper end of the stem, and the mounting element according to claim 1 fastened on the abutment plate.

19. The implant system according to claim 17, wherein the mounting element is screwed to the implant surface and/or abutment plate.

20. The mounting element according to claim 1, further comprising a friction insert.

21. The mounting element of claim 1, wherein a mean distance between a lower end of the first outer ring and a lower end of the mounting element is in the range of 0.3 mm to 0.7 mm.

* * * * *